United States Patent
Yamauchi et al.

(10) Patent No.: US 9,645,122 B2
(45) Date of Patent: May 9, 2017

(54) VIBRATION GENERATION APPARATUS

(71) Applicant: DENSO CORPORATION, Kariya, Aichi-pref. (JP)

(72) Inventors: Shigenori Yamauchi, Nisshin (JP); Takamoto Watanabe, Nagoya (JP); Tomohito Terazawa, Okazaki (JP)

(73) Assignee: DENSO CORPORATION, Kariya (JP)

( * ) Notice: Subject to any disclaimer, the term of this patent is extended or adjusted under 35 U.S.C. 154(b) by 297 days.

(21) Appl. No.: 14/288,436

(22) Filed: May 28, 2014

(65) Prior Publication Data
US 2015/0020596 A1 Jan. 22, 2015

(30) Foreign Application Priority Data
Jul. 17, 2013 (JP) ................. 2013-148537

(51) Int. Cl.
*H03B 5/30* (2006.01)
*G01N 29/34* (2006.01)
*G01P 21/00* (2006.01)
*B06B 1/02* (2006.01)

(52) U.S. Cl.
CPC ........... *G01N 29/34* (2013.01); *B06B 1/0261* (2013.01); *B06B 1/0292* (2013.01); *G01N 29/343* (2013.01); *G01P 21/00* (2013.01); *H03B 5/30* (2013.01)

(58) Field of Classification Search
CPC ... H03H 9/21; H03B 5/30; H03B 5/32; G01C 19/56; G01C 15/097; G01C 19/5705; B81B 2201/0242; B81B 2201/0285; G01P 21/00

USPC ............ 331/154, 96, 57, 116 M; 73/504.14, 73/504.12, 514.32
See application file for complete search history.

(56) References Cited

U.S. PATENT DOCUMENTS

| | | |
|---|---|---|
| 5,128,624 A | 7/1992 | Hoshino et al. |
| 5,289,135 A | 2/1994 | Hoshino et al. |
| 5,428,321 A | 6/1995 | Yoshida et al. |
| 5,477,196 A | 12/1995 | Yamauchi et al. |
| 5,525,939 A | 6/1996 | Yamauchi et al. |
| 5,568,071 A | 10/1996 | Hoshino et al. |
| 2003/0200803 A1 | 10/2003 | Platt |
| 2008/0180872 A1* | 7/2008 | Mishima ........... H01G 5/18 361/139 |
| 2010/0087966 A1 | 4/2010 | Terazawa et al. |
| 2011/0179868 A1 | 7/2011 | Kaino et al. |

(Continued)

FOREIGN PATENT DOCUMENTS

| | | |
|---|---|---|
| JP | 06-283984 A | 10/1994 |
| JP | 07-030388 A | 1/1995 |

OTHER PUBLICATIONS

U.S. Appl. No. 14/288,464, filed May 28, 2014, Yamauchi et al.
Office Action mailed Jun. 23, 2015 in the related JP Application No. 2013-148538 (English translation attached).

*Primary Examiner* — Arnold Kinkead
(74) *Attorney, Agent, or Firm* — Posz Law Group, PLC

(57) ABSTRACT

A gyro sensor includes a vibrator and a drive circuit. A PWM drive signal is applied to a pair of electrodes of the vibrator. The drive circuit outputs a high level signal and a low level signal to the electrodes as the PWM drive signal. The high level signal and the low level signal have potentials higher and lower than that of the reference signal, respectively. The drive circuit outputs the high level signal to one of the pair of electrodes and the low level signal to the other of the pair of electrodes.

7 Claims, 9 Drawing Sheets

(56) References Cited

U.S. PATENT DOCUMENTS

2012/0291550 A1 11/2012 Kato et al.
2013/0207733 A1 8/2013 Yamauchi et al.

* cited by examiner

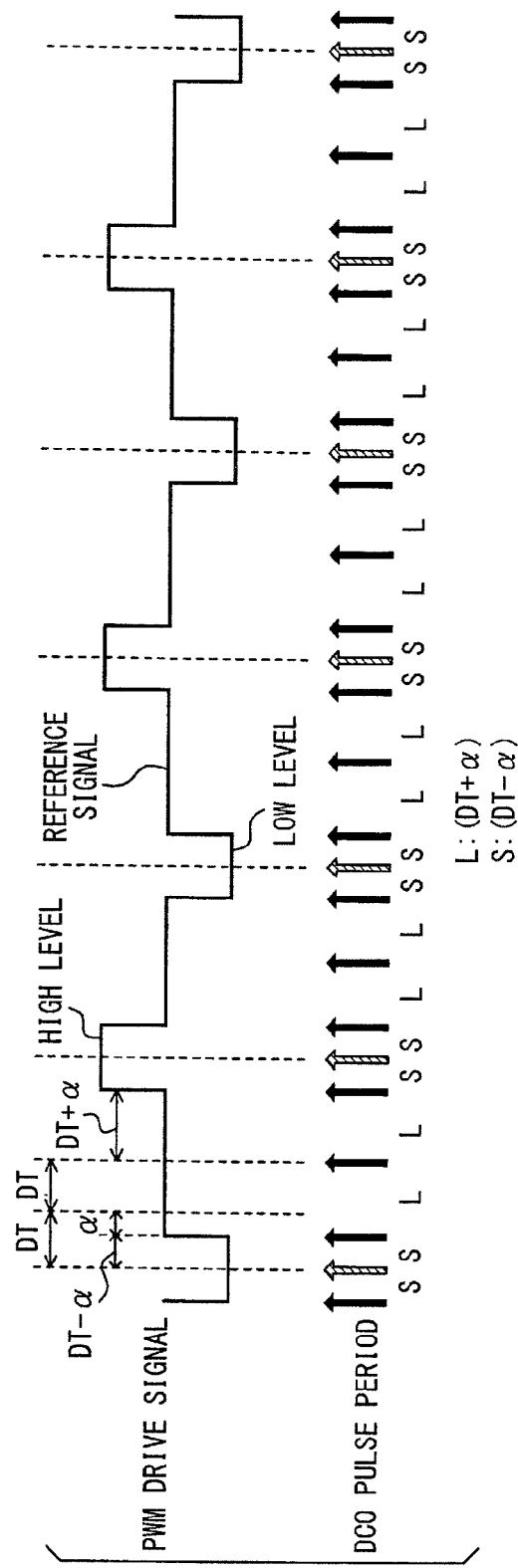

US 9,645,122 B2

VIBRATION GENERATION APPARATUS

CROSS REFERENCE TO RELATED APPLICATION

This application is based on and incorporates herein by reference Japanese patent application No. 2013-148537 filed on Jul. 17, 2013.

FIELD

The present disclosure relates to a vibration generation apparatus, which drives a test body to vibrate by a PWM drive signal.

BACKGROUND

Various conventional systems include vibration generation apparatuses, which drive a test body to vibrate by a PWM (pulse-width modulation) drive signal. Some of the vibration generation apparatuses generate PWM drive signals by comparing an input signal level with a threshold level as disclosed in JP-A-2005-524077 (US2003/0200803 A1), for example.

According to the vibration generation apparatus described above, however, an analog waveform is utilized in comparing the input signal level with the threshold level. The analog signal is likely to be susceptible to noise or the like. If a circuit is provided to reduce influence of noise, the apparatus becomes large-sized.

SUMMARY

It is therefore an object to provide a vibration generation apparatus, which reduces influence of noise in driving a test body to vibrate by a PWM drive signal.

According to one aspect, a vibration generation apparatus is provided for driving a test body to vibrate in response to a PWM drive signal. The vibration generation apparatus comprises a pair of electrodes, which input the PWM drive signal to the test body, and a drive part, which outputs as the PWM drive signal a high level signal and a low level signal to the pair of electrodes. The high level signal and the low level signal have potentials higher and lower than a potential of a reference signal, respectively. The drive part outputs the high level signal and the low level signal to one and the other of the pair of electrodes, respectively.

BRIEF DESCRIPTION OF THE DRAWINGS

FIG. 9 is an explanatory diagram showing a method of generation of a PWM drive signal by a DCO shown in FIG. 5;

DETAILED DESCRIPTION OF THE EMBODIMENT

Figure 1:
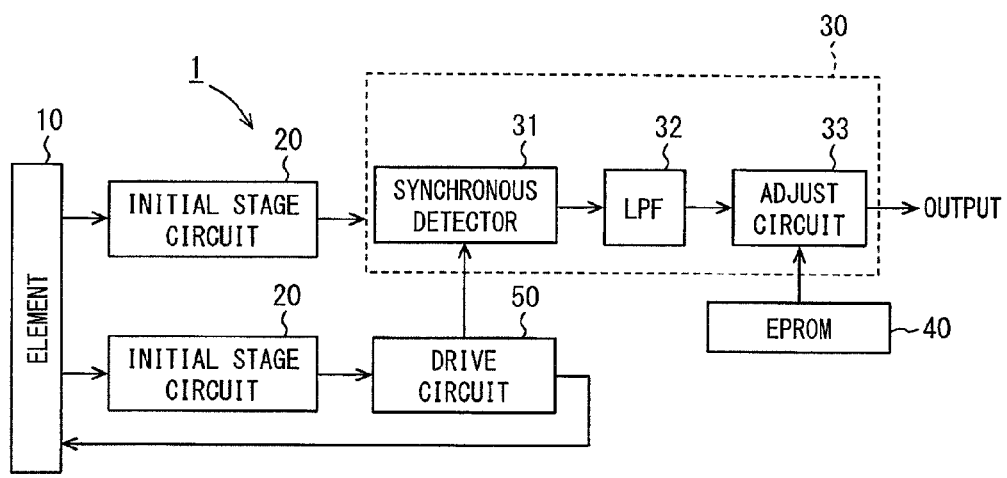
FIG. 1 is a block diagram showing a gyro sensor.

Referring to FIG. 1, a gyro sensor 1 is configured as a vibration generation apparatus for vibrating a test body, that is, driving the test body to vibrate by applying a PWM (pulse-width modulation) drive signal thereto. The gyro sensor 1 is formed of an element 10, two initial stage circuits 20, a signal detection circuit 30, an EPROM 40 and a drive circuit 50. The element 10, the initial stage circuit 20, the signal detection circuit 30 and the EPROM 40 are conventional as used in general gyro sensors. The drive circuit 50 and the initial stage circuit 20 form a self-excited resonant circuit.

Figure 2:
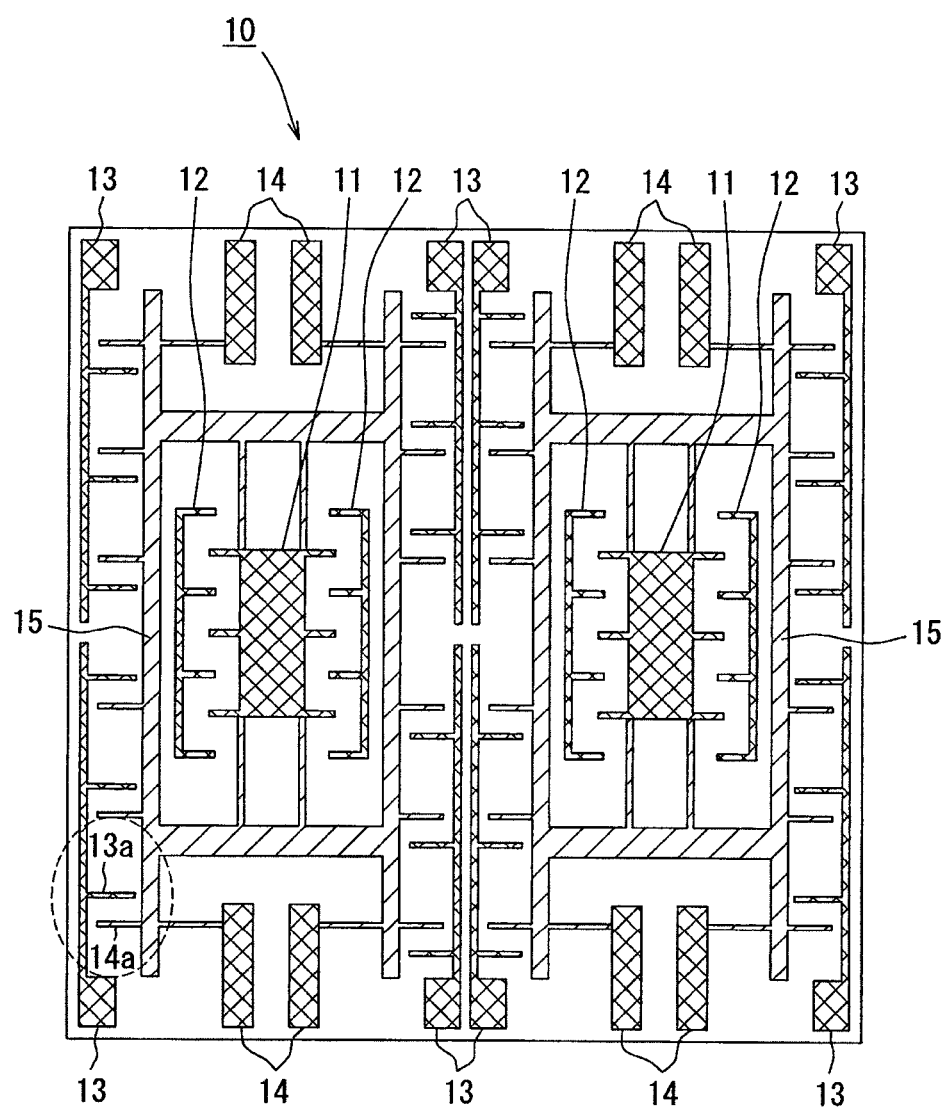
FIG. 2 is a plan view of one example of an element shown in FIG. 1.

In the element 10, a vibrator 11 shown in FIG. 2 displaces to deviate from the direction of vibration in response to external force applied thereto while vibrating. As a result, the electrostatic capacitance varies. The element 10, which is exemplarily shown in FIG. 2 is conventional as used in MEMS gyros.

The element 10 is formed of the vibrator 11, electrodes 12, 13, 14 and a frame 15. The vibrator 11 is supported by the frame 15. When a PWM drive signal is applied to the electrodes 13, 14, electrostatic capacitance is generated between capacitive parts 13a and 14a. This capacitance vibrates the frame 15 in the up-down direction in FIG. 2.

The vibrator 11 vibrates with the frame 15. When external force is applied, the vibrator 11 displaces in the left-right direction in FIG. 2 and varies the electrostatic capacitance between the vibrator 11 and the electrode 12. The element 10 outputs to the initial stage circuit 20 the electrostatic capacitance between the capacitive parts 13a and 14a and the electrostatic capacitance between the vibrator 11 and the electrode 12.

Referring back to FIG. 1, the initial stage circuit 20 includes a CV conversion circuit (not shown). This CV conversion circuit converts the electrostatic capacitance to a voltage signal. The initial stage circuit 20 on the signal detection side, which is connected to the signal detection circuit 30, converts the electrostatic capacitance generated between the vibrator 11 and the electrode 12 to a voltage signal. This voltage signal is an angular velocity signal, on which a voltage variation signal is superimposed. The angular velocity signal indicates an angular velocity of the vibrator 11 of the element 10. The voltage variation signal is generated by the resonance of the element 10. The initial stage circuit 20 on the drive side, which is connected to the drive circuit 50, converts the electrostatic capacitance generated between the capacitive parts 13a and 14a to a voltage signal. In the following description, the voltage signal outputted from the initial stage circuit 20 on the drive side is referred to as a drive detection signal and the drive signal outputted from the initial stage circuit 20 on the signal detection side is referred to as a displacement detection signal.

The signal detection circuit 30 extracts the angular velocity signal from the displacement detection signal inputted from the initial stage circuit 20 to provide an output indicative of behavior of the vibrator 11. The signal detection circuit 30 includes a synchronous detector 31, a LPF (low-pass filter) 32 and an amplification adjust circuit 33. The drive signal generated by the drive circuit 50 is inputted to the synchronous detector 31 as a reference signal. The synchronous detector 31 performs synchronous detection by using the reference signal thereby to remove signal components of a drive signal period from the displacement detection signal.

Figure 3:
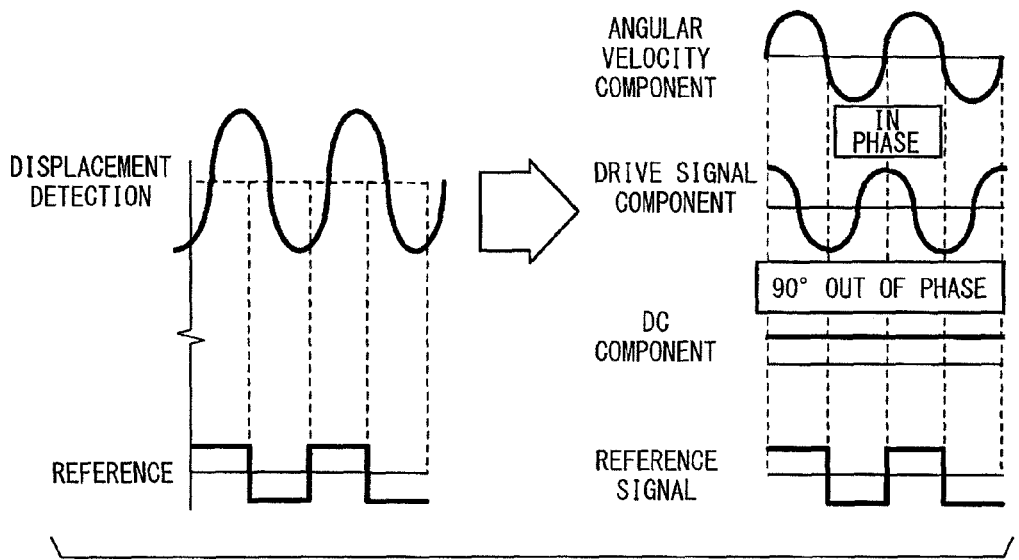
FIG. 3 is a waveform diagram showing signal components of a displacement detection signal when the element is in a resonance state.
Figure 4:
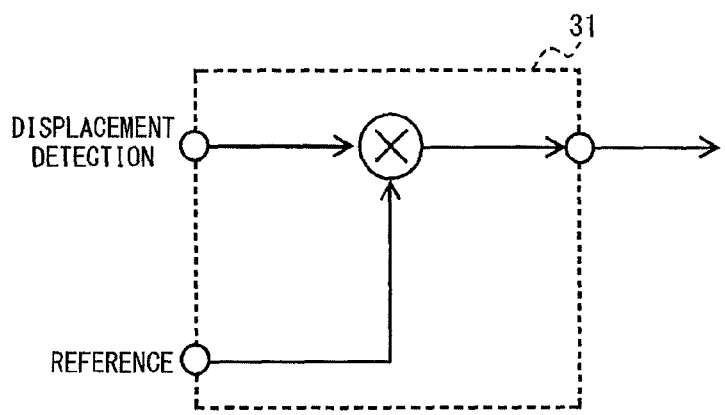
FIG. 4 is an explanatory diagram showing a synchronous detector circuit shown in FIG. 1.

As shown in FIG. 3, the displacement detection signal is separated into the angular velocity signal, the drive signal component and a DC component (direct current component). It is known in the art that a phase of an output signal of the element deviates about 90° relative to external force applied to the element in a resonance state. In an example shown in FIG. 3 as well, the drive signal component, which is the output signal component generated when the vibrator 11 vibrates in response to the drive signal, is 90° out of phase relative to the drive signal inputted as the reference signal.

For this reason, the synchronous detector 31 multiplies the displacement detection signal and the reference signal. Thus the drive signal component, which has the phase deviation of about 90° relative to the reference signal, is removed from the displacement detection signal.

Referring back to FIG. 3, the signal detected by the synchronous detector 31 is subjected to removal of high frequency components by the LPF 32 and then to sensitivity correction and signal amplification by the amplification adjustment part 33. A sensitivity correction coefficient is stored in the EPROM 40.

Figure 5:
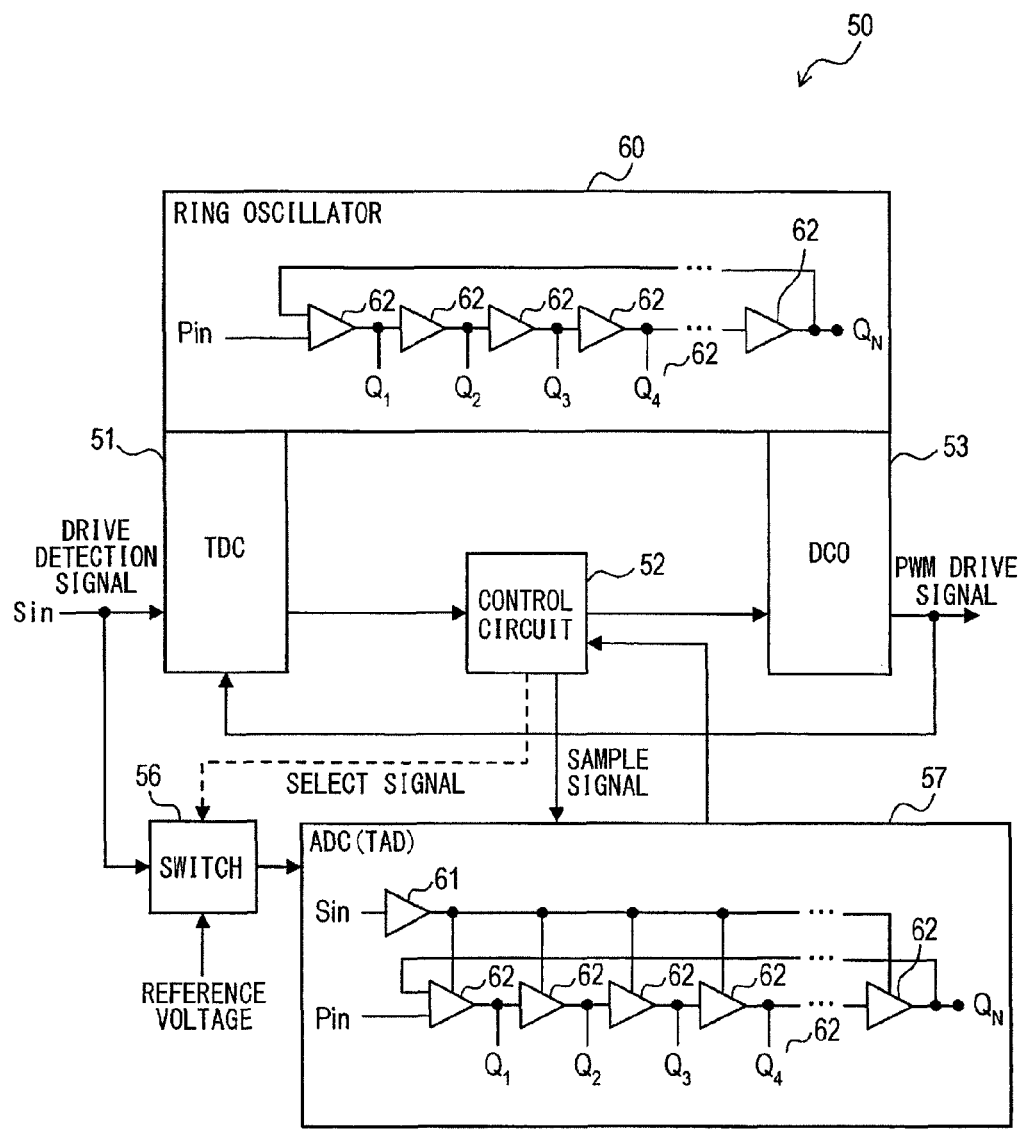
FIG. 5 is a detailed diagram of a drive circuit shown in FIG. 1.

The configuration of the drive circuit 50 will be described next. As shown in FIG. 5, the drive circuit 50 includes a time-to-digital converter (TDC) 51, a digitally-controlled oscillator (DCO) 53, the control circuit 52, a switch 56, a time A/D converter (ADC(TAD)) 57 and a ring oscillator 60. The control circuit 52 may be a microcomputer, which performs various programmed processing.

The ring oscillator 60 is a digital oscillation circuit. This ring oscillator 60 may be configured as disclosed in, for example, JP-A-H07-183800 (U.S. Pat. No. 5,477,196 A). That is, the ring oscillator 60 includes a plurality of gate circuits 62 such as inverters connected in a ring form so that an input signal (Pin) inputted as a pulse signal is inverted by each gate circuit 62 and circulated to return to the gate circuit 62, to which the input signal is inputted.

From a plurality of output terminals Q1 to QN, each of which corresponds to each gate circuit 62, signals, each of which corresponds to an inversion operation time (gate delay time) of the gate circuit 62, are outputted. The signals outputted from the plural output terminals Q1 to QN are inputted to the TDC 51 and the DCO 53.

The drive detection signal is inputted to the TDC 51 from the initial stage circuit 20. The drive signal is fed back from the DCO 53 and inputted to the TDC 51. The TDC 51 detects the phase difference of the drive detection signal relative to the drive signal (that is, phase delay of the drive detection signal relative to the drive signal) as digital time information.

This phase difference is detected by measuring a time difference from a pulse rise time of the drive signal to a pulse rise time of the drive detection signal (rise time of a signal produced by digitizing the drive detection signal by a comparator or the like). In measuring the time difference, the TDC 51 uses the pulse signal generated by the ring oscillator 60 as a clock pulse. That is, the TDC 51 counts the pulse signal, which is generated by the ring oscillator 60 during a period from the pulse rise time of the drive signal to the pulse rise time of the drive detection signal, and calculates the phase difference based on the count value.

The DCO 53 outputs the drive signal at an interval corresponding to a control signal inputted from the control circuit 52. In determining the interval, the DCO 53 uses the pulse signal generated by the ring oscillator 60 as a clock pulse. The drive signal outputted by the DCO 53 is inputted to the element 10 and also to the TDC 51. The DCO 53 may be configured as disclosed in JP-A-H07-106923 (U.S. Pat. No. 5,525,939 A). Use of the clock pulse of the same ring oscillator 60 is conventional as disclosed in JP-A-H07-183800 (U.S. Pat. No. 5,477,196 A) and the like and hence detailed description is not made here.

The control circuit 52 controls the interval of the drive signal (that is, frequency of the drive signal) so that the phase difference detected by the TDC 51 becomes a predetermined resonant phase difference. This control is performed by outputting the control signal, which is a digital signal, to the DCO 53. The resonant phase difference means a phase difference between a phase of the external force and a phase of vibration of an object in a state that the object is in resonance. It is known that this resonant phase difference is about 90°. However this resonant phase difference may deviate slightly from 90° due to various conditions. The resonant phase difference is, for example, 87° as a specific value.

The control circuit 52 controls the frequency of the drive signal, because it is known that the deviation of the vibration phase of the vibrator 11 (phase of the drive detection signal) relative to the phase of the external force inputted to the vibrator 11 (phase of the drive signal) depends on the frequency. Specifically, in a case that the frequency is lower than the resonant frequency, the phase delay of the vibration phase of the vibrator relative to the phase of the external force becomes smaller than the resonant phase difference, which is about 90°. In a case that the frequency is higher than the resonant frequency, the phase delay of the vibration phase of the vibrator relative to the phase of the external force becomes larger than the resonant phase difference. For this reason, the detected phase difference can be adjusted by increasing or decreasing the frequency of the drive signal. It is noted that, in a case that the phase delay is smaller and larger than the resonant phase difference, the two phases are in-phase and anti-phase, respectively.

Since the detected phase difference can be adjusted by thus increasing and decreasing the frequency of the drive signal, the control circuit 52 performs frequency adjustment processing as described later. That is, the frequency is increased when the detected phase difference is smaller than the resonant phase difference. Thus the detected phase difference becomes larger and approaches the resonant phase difference. On the contrary, the frequency is decreased when the detected phase difference is larger than the resonant phase difference. Thus the detected phase difference becomes smaller and approaches the resonant phase difference.

The switch 56 selects either one of the drive detection signal and two kinds of reference voltages in response to a select signal outputted by the control circuit 52 and outputs the selected signal to the ADC 57. The ADC 57 is formed as an ADC of a variable input power voltage type and includes a plurality of gate circuits 62 similarly to the ring oscillator 60 described above. The ADC 57 outputs a count value corresponding to a voltage (input voltage) of the drive detection signal as a digital value in accordance with a sampling signal outputted from the control circuit 52. The ADC 57 thus operates as a time A/D converter (TAD).

The TAD is conventional and not described in detail here. In the ADC 57, the drive detection signal (Sin) is inputted as a power voltage of each gate circuit 62 through a buffer 61. The inversion operation time in each gate circuit 62 varies with a voltage level of the drive detection signal. Signals outputted from the plural output terminals Q1 to QN are inputted to the control circuit 52.

Figure 6:
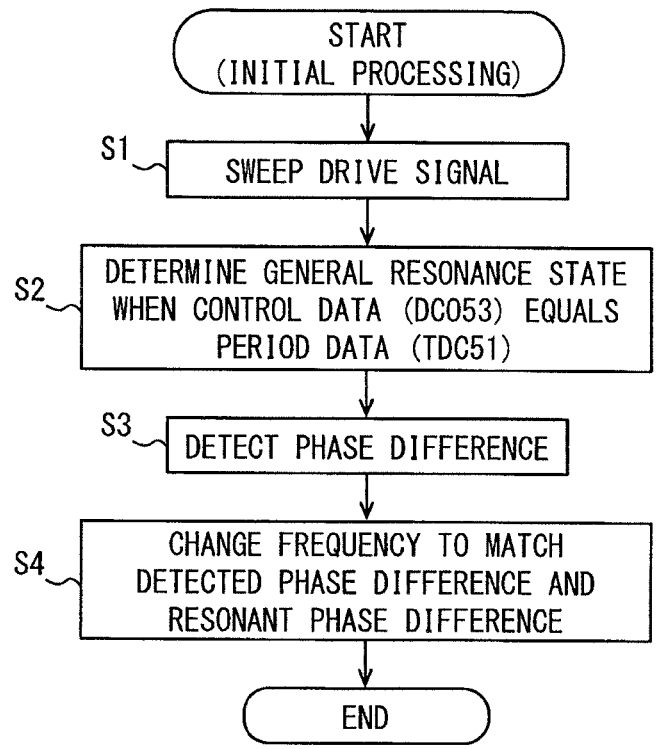
FIG. 6 is a flowchart showing initial processing performed by a control circuit shown in FIG. 5.

The control circuit 52 performs, before the above-described frequency adjustment processing, initial processing, which is general resonance control processing, so that the vibrator 11 of the element 10 is driven to general resonance state. The initial processing of the control circuit 52 is performed in the initial operation as shown in FIG. 6 at the time of starting measurement, for example. The drive detection signal does not contain the angular velocity signal component and hence the phase of the drive detection signal is considered to be a signal originating from the drive signal component.

In the initial processing, the general resonance control processing described above is executed first (S1, S2). That is, the drive signal outputted from the DCO 53 is swept (S1). Sweeping covers a range from a frequency sufficiently lower than the resonant frequency of the element 10 to a frequency sufficiently higher than the resonant frequency. Sweeping the frequency is finished at a time point when it is determined to be the general resonance state. In a case that the ring oscillator 60 includes gate delay circuits, the ring oscillator 60 has temperature characteristics. For this reason, at S1, temperature compensation is performed so that the frequency of the drive signal is swept from the lowest limit to the highest limit irrespective of ambient temperatures.

Subsequently, it is determined that the vibrator 11 of the element 10 is in the general resonance state. Specifically, the vibrator 10 is determined to be in the general resonance state when the phase difference detected by the TDC 51 is within a predetermined general resonance range, which is considered to correspond to the general resonance state. The general resonance range is, for example, from 90% to 110% of the resonant phase difference. When the general resonance state is established in the course of sweeping the frequency of the drive signal, an amplitude of a waveform of the drive detection signal becomes large rapidly. For this reason, in a case that the A/D converter (ADC 57 or the like) is provided for converting the drive detection signal to a digital signal, the general resonance state may be determined based on the amplitude of a signal outputted from the A/D converter. S3 is executed after determination of the general resonance state.

Subsequently, the frequency adjustment processing described above is executed. That is, the phase difference between the drive signal and the drive detection signal is detected. Specifically, a signal indicating the phase difference is taken out from the TDC 51.

Then the frequency of the drive signal is changed so that the detected phase difference match the resonant phase difference (S4). Specifically, when the detected phase difference is smaller and larger than the resonant phase difference, the frequency of the drive signal is increased and decreased by a predetermined value, respectively. After changing the frequency of the drive signal, S3 is executed to detect the phase difference again.

When it is determined that the detected phase difference equals the resonant phase difference, the frequency is not changed. When the frequency is not changed, S3 may be executed again to continue monitoring of the phase difference. Alternatively, the initial processing of FIG. 6 may be finished. When the initial processing is finished, the self-excited resonance state of the vibrator 11 is maintained by continuing the processing corresponding to S3 and S4 while detecting the angular velocity signal component.

Figure 7:
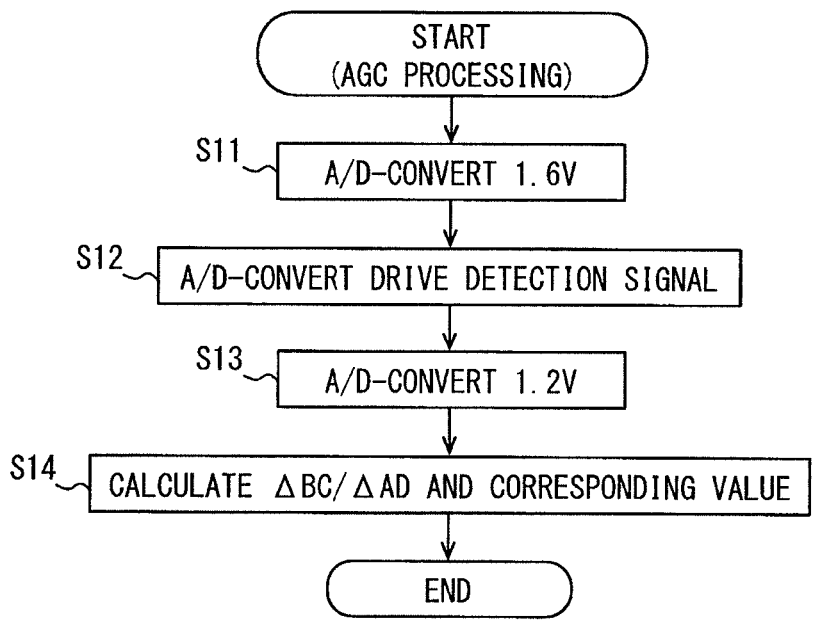
FIG. 7 is a flowchart showing AGC processing performed by the control circuit.

The control circuit 52 performs AGC (automatic gain control) processing shown in FIG. 7 separately from the initial processing shown in FIG. 6. The AGC processing is started at every predetermined interval or at every change of the ambient temperature in excess of a predetermined reference value of change. This processing is for controlling the duty ratio of the PWM drive signal so that the magnitude of vibration of the vibrator 11 is maintained at a predetermined magnitude level. In S11 to S13, the processing of the A/D conversion is continued for a period set for each processing.

In the AGC processing, as shown in FIG. 7, the reference voltage of 1.6V is A/D-converted first (S11). In this step, a select signal, which indicates an input of the first reference voltage (1.6V), is outputted to the switch 56 so that the first reference voltage is inputted to the ADC 57 through the switch 56.

The control circuit 52 also has a configuration of the synchronous detection similarly to the synchronous detector 31. The control circuit 52 is configured to synchronously detect the drive signal and the drive detection signal so that the vibration phase of the vibrator 11 is detected. The control circuit 52 outputs a sampling signal to the ADC 57 at time points when the vibration phase becomes 0° and 180°, that is, at every interval of ½ cycle period. The ADC 57 outputs the digital value based on the count value of the ring oscillator between two sampling signals.

This digital value corresponds to integration of changes of the voltage value between the sampling signals. The resolving power is the gate delay time. The digital value at this time corresponds to A shown in FIG. 8.

Subsequently, the drive detection signal Sin is A/D-converted (S12). In this step, a selecting signal, which indicates an input of the drive detection signal, is outputted to the switch 56 so that the drive detection signal is inputted to the ADC 57 through the switch 56. The ADC 57 thus outputs a digital value, which corresponds to an average voltage thereof at every ½ cycle period of the drive detection signal. That is, the digital value at this time becomes a value, which is averaged at every ½ cycle period of the drive detection signal. This digital value corresponds to B and C shown in FIG. 8.

Subsequently, the reference voltage of 1.2V is A/D-converted (S13). In this step, a selecting signal, which indicates an input of the second reference voltage (1.2V), is outputted to the switch 56 so that the second reference voltage is inputted to the ADC 57 through the switch 56. The ADC 57 thus outputs a digital value, which corresponds to D shown in FIG. 8.

Figure 8:
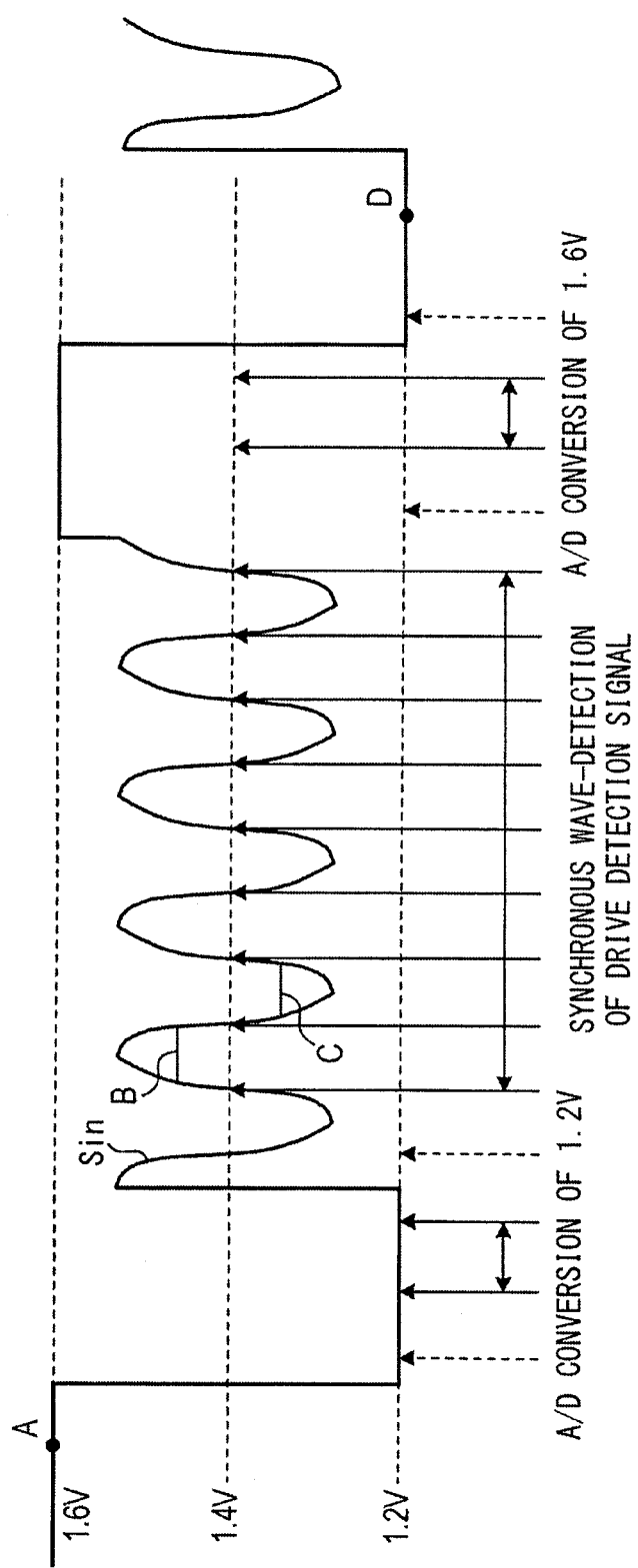
FIG. 8 is a waveform diagram showing in detail a drive detection signal at the AGC processing time.

In the flowchart shown in FIG. 7, the first reference voltage (1.6V), the drive detection signal and the second reference voltage (1.2V) are sampled in this order. In the example of FIG. 8, however, the first reference voltage (1.6V), the second reference voltage (1.2V) and the drive detection signal are sampled in this order. This order of sampling may be arbitrarily determined.

Subsequently, a ratio ΔBC/ΔAD of a difference of potentials in the drive detection signal (potential difference ΔBC between B and C in FIG. 8) to a difference of potentials of the reference voltage (potential difference ΔAD between A and D in FIG. 8) is calculated (S14). Then the duty ratio of the PWM drive signal is set so that the calculated ratio is maintained at a constant value. The potential difference of the drive detection signal, which is smaller than a target value, indicates that the magnitude of vibration of the vibrator 11 is smaller than the target value. Therefore, the duty ratio is set to increase the magnitude of the frame 15. The potential difference of the drive detection signal, which is larger than the value of the target ratio, indicates that the magnitude of vibration of the vibrator 11 is larger than the target value. Therefore, the duty ratio is set to decrease the magnitude of vibration.

The control circuit 52 calculates, at S14, a count value DT of the ring oscillator 60, which corresponds to ⅛ period of the vibration period of the vibrator 11, so that the phase difference between the drive signal and the drive detection signal becomes the resonant phase difference. The control circuit 52 calculates a value $\alpha$, with which the duty ratio for making the ratio between the potential difference of the drive detection signal and the potential difference of the reference voltage constant becomes $(DT-\alpha)/DT$. The control circuit 52 thus outputs eight values to the DCO 53 in one cycle period. Those values are outputted in the order of $(DT-\alpha)$, $(DT-\alpha)$, $(DT+\alpha)$, $(DT+\alpha)$, $(DT-\alpha)$, $(DT-\alpha)$, $(DT+\alpha)$, $(DT+\alpha)$ and the like.

As shown in FIG. 9, the DCO 53 outputs to the electrode 13, for example, the low level signal, which is lower than the potential of the reference signal, as the first two output signals (pulses). The DCO 53 outputs the reference signal of the reference potential as the next two output signals. The DCO 53 outputs the high level signal, which is higher than the potential of the reference signal, as the further next two output signals. The DCO 53 outputs the reference signal as the last two output signals.

The DCO 53 generates, in response to the above-described output signals from the control circuit 52, the PWM drive signal by continuously outputting the signal of each level for a period, which corresponds to the count value $((DT-\alpha)$ or $(DT+\alpha))$ of the ring oscillator 60 designated by the control circuit 52. This configuration outputs the pulse (even-numbered pulse), which corresponds to the vibration phase, and the pulse (odd-numbered pulse), which corresponds to the duty ratio. The DCO 53 thus outputs at least eight pulses in one cycle period of change of the waveform phase (vibration phase).

Figure 10A:
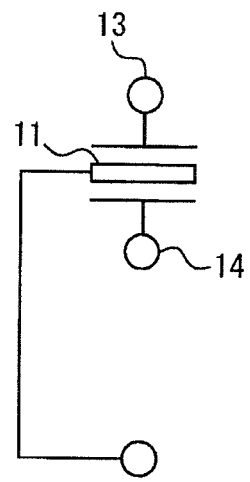
FIGS. 10A, 10B and 10C are schematic views of a vibration body and electrodes, a waveform diagram showing one example of the PWM drive signal, and a waveform diagram showing coupling noise, respectively.
Figure 10B:
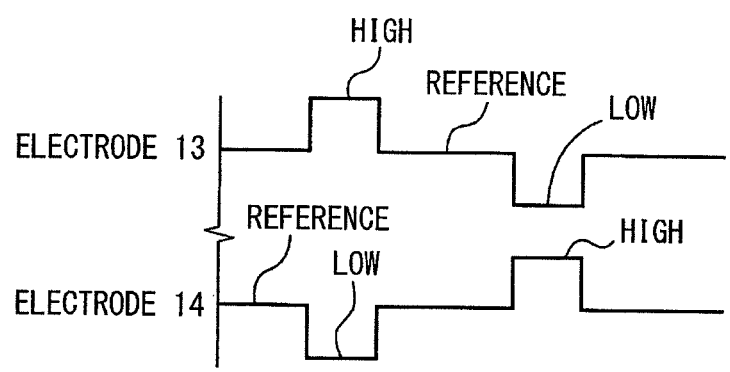
Figure 10C:

The drive circuit 50 (DCO 53) applies a first PWM drive signal shown in FIG. 9 to one electrode (first electrode) 13 of the pair of electrodes 13, 14 (FIG. 10A), to which the PWM drive signal is applied to vibrate the vibrator 11. The drive circuit 50 also applies a second PWM drive signal to the other electrode (second electrode) 14. The second PWM drive signal is of opposite polarity to the first PWM drive signal. That is, as shown in FIG. 10B, when the high level signal is being applied to the first electrode 13, the low level signal is being applied to the second electrode 14. Both of the first PWM drive signal and the second PWM drive signal takes a reference potential level of the reference signal between the high level signal and the low level signal. Thus coupling noise is reduced as shown in FIG. 10C. The AGC processing is finished when the signals are outputted as described above.

The above-described embodiment has the following features and advantages.

The gyro sensor 1 has a pair of electrodes 13 and 14, to which the PWM drive signal is applied in the vibrator; and the drive circuit 50, which outputs, as the PWM drive signal, the high level signal and the low level signal to the pair of electrodes 13 and 14. The high level signal and the low level signal have potentials higher and lower than the potential of the reference signal, respectively. The drive circuit 50 outputs the high level signal and the low level signal to one and the other of the pair of electrodes 13 and 14, respectively. Since the high level signal and the low level signal are outputted to the pair of electrodes 13 and 14, noises generated by those signals can be cancelled. As a result, influence of noise can be reduced.

The gyro sensor 1 has the TDC 51 (including the ring oscillator 60), which detects the phase difference between the waveform phase of the PWM drive signal and the vibration phase of the vibrator 11. The dive circuit 50 (excluding the TDC 51) outputs the phase-adjusted drive signal so that the phase difference becomes the predetermined phase difference. The phase difference between the waveform phase of the PWM drive signal and the vibration phase of the vibrator 11 can be controlled to the predetermined phase difference.

Further, since the TDC 51 outputs the digital value corresponding to the phase difference, more anti-noise performance can be provided.

The drive circuit 50 (excluding the TDC 51) outputs the phase-adjusted drive signal so that the phase difference between the waveform phase of the PWM drive signal and the vibration phase of the vibrator 11 becomes the phase difference, which causes the self-excited resonance of the vibrator 11. Since the vibrator 11 resonates by self-excitation, the energy supplied to the vibrator 11 can be minimized and the vibrator 11 can be driven to vibrate efficiently.

The drive circuit 50 (excluding the TDC 51) outputs the phase-adjusted drive signal so that the vibration phase has a phase delay of 90° or about 90° relative to the waveform phase. The vibrator 11 can be driven to resonate by self-excitation.

The TDC 51 detects the phase difference based on the gate delay time of the ring oscillator 60, in which the plurality of gate circuits 62 are connected in series in the ring form. The gate delay time indicates the delay time of each gate. Since the phase difference can be detected with the resolving power of the gate delay time, the accuracy of the phase difference detection can be increased.

The signal detection circuit is provided for producing the output based on the behavior of the vibrator 11. Since the output value is provided in correspondence to the behavior of the vibrator 11 (for example, Coriolis force applied to the vibrator 11), the gyro sensor 1 can be used to function as a sensor.

The TDC 51 detects the magnitude of vibration of the vibrator 11. The drive circuit 50 (excluding the TDC 51) determines the duty ratio of the PWM drive signal so that the magnitude becomes the predetermined magnitude in accordance with the magnitude of vibration of the vibrator 11. The drive circuit 50 outputs the PWM drive signal of the determined duty ratio. The drive circuit 50 (excluding the TDC 51) includes the control circuit 52 and the DCO 53. The control circuit 52 outputs the control value corresponding to the target duty ratio of the PWM drive signal. The DCO 53 generates the PWM drive signal, which has the pulse width corresponding to the inputted control value and generates the PWM drive signal, by performing time measurement based on the gate delay time in accordance with the control value. Since the PWM drive signal having the pulse width corresponding to the inputted control value is generated by measuring time based on the gate delay time, the processing of generating the PWM drive signal can be performed by digital processing. As a result, in comparison to the case of generation of the PWM drive signal by analog processing, influence of noise can be reduced.

The DCO 53 generates the PWM drive signal by using the pulse generated by the ring oscillator 60 having the plurality of gate circuits 62 connected in series in the ring form. The pulse is generated based on the gate delay time, which indicates the delay time of each gate circuit 62. Since the PWM drive signal having the pulse width, the resolving power of which is the gate delay time, the PWM drive signal can be outputted with higher accuracy.

The DCO 53 uses the same ring oscillator 60 as the TDC 51 (ring oscillator 60) uses and generates the PWM drive signal by using the pulse generated based on the gate delay time provided by the ring oscillator 60. The DCO 53 and the TDC 51 (ring oscillator 60) can have the common resolving power. The signal processing can be simplified.

The DCO 53 outputs, as the PWM drive signal, the pulse corresponding to the waveform phase and the pulse corresponding to the duty ratio. The phase of the drive signal can be outputted by the pulse corresponding to the waveform phase in outputting the PWM drive signal.

The DCO 53 outputs the pulses at least eight times in the period, in which the waveform phase changes one cycle period. The PWM drive signal can be generated while outputting the signal indicating the phase of the drive signal appropriately.

The ADC 57 generates not only the amplitude digital value corresponding to the magnitude of the vibration waveform of the vibrator 11 but also the voltage digital value corresponding to the difference between the two different reference voltages. The drive circuit 50 (excluding TDC 51) generates the drive signal so that the ratio between the voltage digital value and the amplitude digital value becomes constant. Since the amplitude of the vibration waveform can be processed digitally, influence of noise can be reduced in comparison to the configuration of analog processing. Since the drive signal is generated so that the ratio between the difference (voltage digital value) of the reference voltages and the amplitude digital value corresponding to the magnitude of the vibration waveform is maintained constant, the drive signal can be generated appropriately even in a case that the configuration for A/D conversion is affected by the environmental condition such as temperature.

Figure 11A:
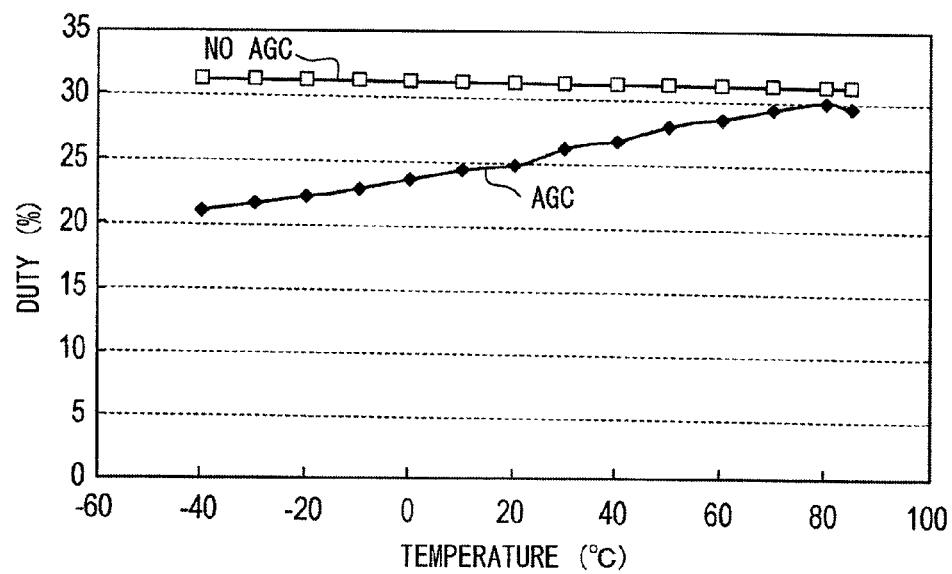
FIGS. 11A and 11B are graphs showing effects of the AGC processing on a duty ratio and an amplitude, respectively.
Figure 11B:
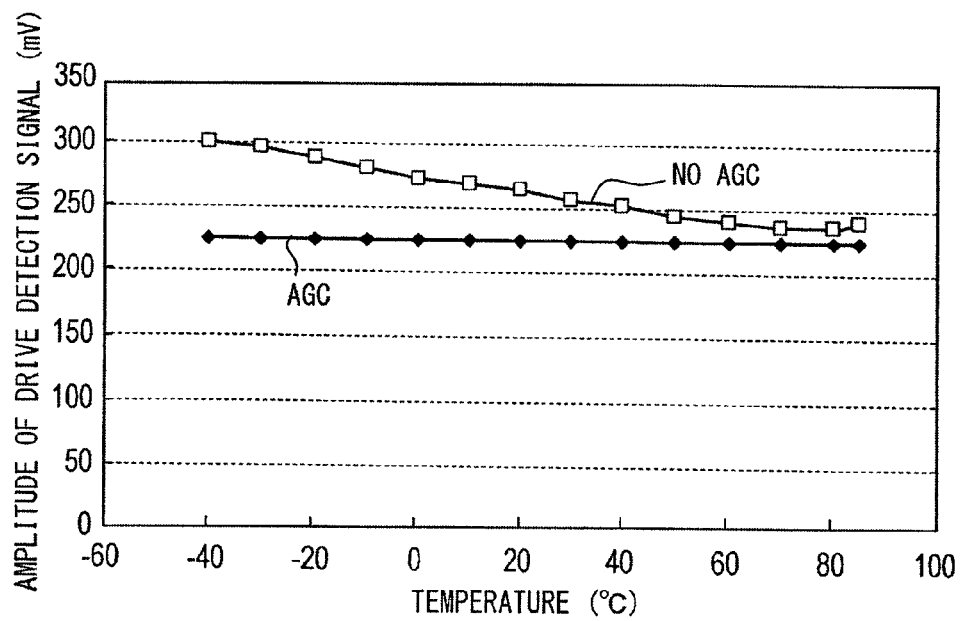

FIGS. 11A and 11B shows a result of comparison between a case (AGC) that the AGC processing is performed as in the present embodiment and a case (NO AGC) that no AGC processing is performed. It is understood that, in the case of no AGC processing, the duty ratio of the PWM drive signal is not changed from the constant value (FIG. 11A) but the amplitude of the drive detection signal is varied in accordance with temperature (FIG. 11B). In the case of AGC processing as in the present embodiment, the duty ratio of the PWM drive signal is feedback-controlled in accordance with the amplitude of the drive detection signal. As a result, the duty ratio of the PWM drive signal varies with temperature (FIG. 11A) and the amplitude of the drive detection signal remains to be constant.

The ADC 57 detects an average value of the vibration waveform in a former half period of the waveform and an average value of the same in a latter half period and sets the difference of these average values as the amplitude digital value. The amplitude can thus be detected with high accuracy.

The ADC 57 is configured as the time A/D converter (which outputs the input voltage as the digital value corresponding to the gate delay time). The A/D conversion can be performed in simple configuration. The ADC 57 sets the sampling time point by using the synchronous detection. The sampling time point can be set more accurately. The ADC 57 generates, at every regular interval or at irregular interval, the voltage digital value corresponding to the difference between the two different reference voltages. Since the voltage digital value can be generated repetitively when necessary, it is possible to respond flexibly to changes in the environmental condition such as temperature.

The switch 56 is provided to select and output the vibration waveform of the vibrator 11 or either one the reference voltages and the ADC 57 integrates the inputted signal. The control circuit 52 (drive circuit 50) switches over the switch 56 at every predetermined time point. The ADC 57 samples the vibration waveform when the vibration waveform of the vibrator 11 is selected by the switch 56. The ADC 57 samples the reference voltage when either one of the reference voltages is selected by the switch 56. Since the ADC 57 switches over the signal to be A/D-converted to the reference voltage or the vibration waveform, the vibration waveform can be detected while appropriately correcting this characteristics even when the characteristics of the ADC 57 changes in accordance with the environmental condition such as temperature.

The ADC 57 sequentially samples the one reference voltage (high level), the vibration waveform and the other reference voltage (low level) in this order. The vibration waveform can be detected accurately even when the reference voltage has certain variations.

The embodiment described above may be modified. For example, in the AGC processing according to the embodiment, two reference voltages (1.6V and 1.2V) are provided and the difference between the two voltages is calculated. However, only one reference voltage may be provided and a voltage such as an average voltage of the drive detection signal (center voltage of the amplitude) may be used as another reference voltage.

In the embodiment, the gyro sensor 1 corresponds to the vibration generation apparatus and the vibrator 11 corresponds to the test body. The drive circuit 50 (excluding TDC 51) corresponds to a drive part, the TDC 51 and the ring oscillator 60 correspond to a phase difference detection part and the gate circuit 62 corresponds to a gate. The DCO 53 corresponds to a drive signal generation circuit and the signal detection circuit corresponds to a behavior output part.

What is claimed is:

1. A vibration generation apparatus for driving a test body to vibrate in response to a PWM drive signal, the vibration generation apparatus comprising:
   a pair of electrodes for inputting the PWM drive signal to the test body;
   a drive part outputting, as the PWM drive signal, a high level signal and a low level signal to the pair of electrodes, the high level signal and the low level signal having potentials higher and lower than a potential of a reference signal, respectively; and
   a phase difference detection part for detecting a phase difference between a waveform phase of the PWM drive signal and a vibration phase of the test body,
   wherein the drive part outputs the high level signal and the low level signal to one and the other of the pair of electrodes, respectively, and
   wherein the drive part outputs a phase-adjusted drive signal so that the phase difference becomes a predetermined phase difference.

2. The vibration generation apparatus according to claim 1, wherein:

the drive part outputs a phase-adjusted drive signal so that the phase difference becomes a phase difference, which causes a self-excited resonance of the test body.

3. The vibration generation apparatus according to claim 1, wherein:
the drive part outputs a phase-adjusted drive signal so that the vibration phase has a phase delay of about 90° relative to the waveform phase.

4. The vibration generation apparatus according to claim 1, wherein:
the phase difference detection part detects the phase difference based on an output value of a ring oscillator having a plurality of gates connected in series in a ring form, the output value being corresponding to a gate delay time, which indicates a delay time of each gate.

5. A vibration generation apparatus for driving a test body to vibrate in response to a PWM drive signal, the vibration generation apparatus comprising:
a pair of electrodes for inputting the PWM drive signal to the test body;
a drive part outputting, as the PWM drive signal, a high level signal and a low level signal to the pair of electrodes, the high level signal and the low level signal having potentials higher and lower than a potential of a reference signal, respectively;
a control circuit for outputting a control value corresponding to a target duty ratio of the PWM drive signal; and
a drive signal generation circuit for generating the PWM drive signal having a pulse width corresponding to an inputted control value and generating the PWM drive signal, by performing time measurement based on the gate delay time in accordance with the control value,
wherein the drive part outputs the high level signal and the low level signal to one and the other of the pair of electrodes, respectively.

6. The vibration generation apparatus according to claim 5, wherein:
the drive signal generation circuit generates the PWM drive signal by using a pulse generated by a ring oscillator having a plurality of gates connected in series in a ring form, the pulse being generated based on a gate delay time, which indicates a delay time of each gate.

7. The vibration generation apparatus according to claim 5, further comprising:
a phase difference detection part for detecting a phase difference between a waveform phase of the PWM drive signal and a vibration phase of the test body,
wherein the drive signal generation circuit uses the ring oscillator, which the phase difference detection part uses, and generates the PWM drive signal by using the pulse generated based on the gate delay time provided by the ring oscillator.

* * * * *